(12) United States Patent   (10) Patent No.: US 6,264,667 B1
McGuckin, Jr.   (45) Date of Patent: Jul. 24, 2001

(54) BLADDER DIALYSIS URINARY CATHETER

(75) Inventor: James F. McGuckin, Jr., Radnor, PA (US)

(73) Assignee: Rex Medical, Radnor, PA (US)

( * ) Notice: Subject to any disclaimer, the term of this patent is extended or adjusted under 35 U.S.C. 154(b) by 0 days.

(21) Appl. No.: 09/122,480

(22) Filed: Jul. 23, 1998

Related U.S. Application Data

(60) Provisional application No. 60/053,557, filed on Jul. 24, 1997.

(51) Int. Cl.$^7$ ..................................... A61B 17/32
(52) U.S. Cl. .......................... 606/167; 606/159; 606/180; 606/192; 604/22; 604/96.01
(58) Field of Search ..................................... 606/159, 167, 606/171, 170, 185, 180, 191–200; 604/19, 22, 96.01

(56) References Cited

U.S. PATENT DOCUMENTS

| | | |
|---|---|---|
| 4,167,944 | 9/1979 | Banko . |
| 4,850,957 | 7/1989 | Summers . |
| 5,002,549 | * 3/1991 | Nash ..................................... 606/128 |
| 5,609,602 | 3/1997 | Machemer et al. . |
| 5,779,722 | * 7/1998 | Shturman et al. .................... 606/180 |
| 5,823,990 | * 10/1998 | Henley ................................. 606/180 |
| 5,860,994 | * 1/1999 | Yaacobi ................................ 606/166 |

* cited by examiner

*Primary Examiner*—Glenn K. Dawson

(57) ABSTRACT

An irrigating bladder dethrombulator for removing blood clots in the urine. The device includes a housing having an outflow conduit insertable into the bladder through the urethra for transporting bodily fluid from the bladder and a bladder pressurization conduit for transporting fluid into the bladder to increase the internal pressure of the bladder. Connected to the housing is structure for mechanically reducing the size of the blood clots in the urine. The mechanism for driving the reducing structure can be a magnetic drive or a fluid drive.

40 Claims, 5 Drawing Sheets

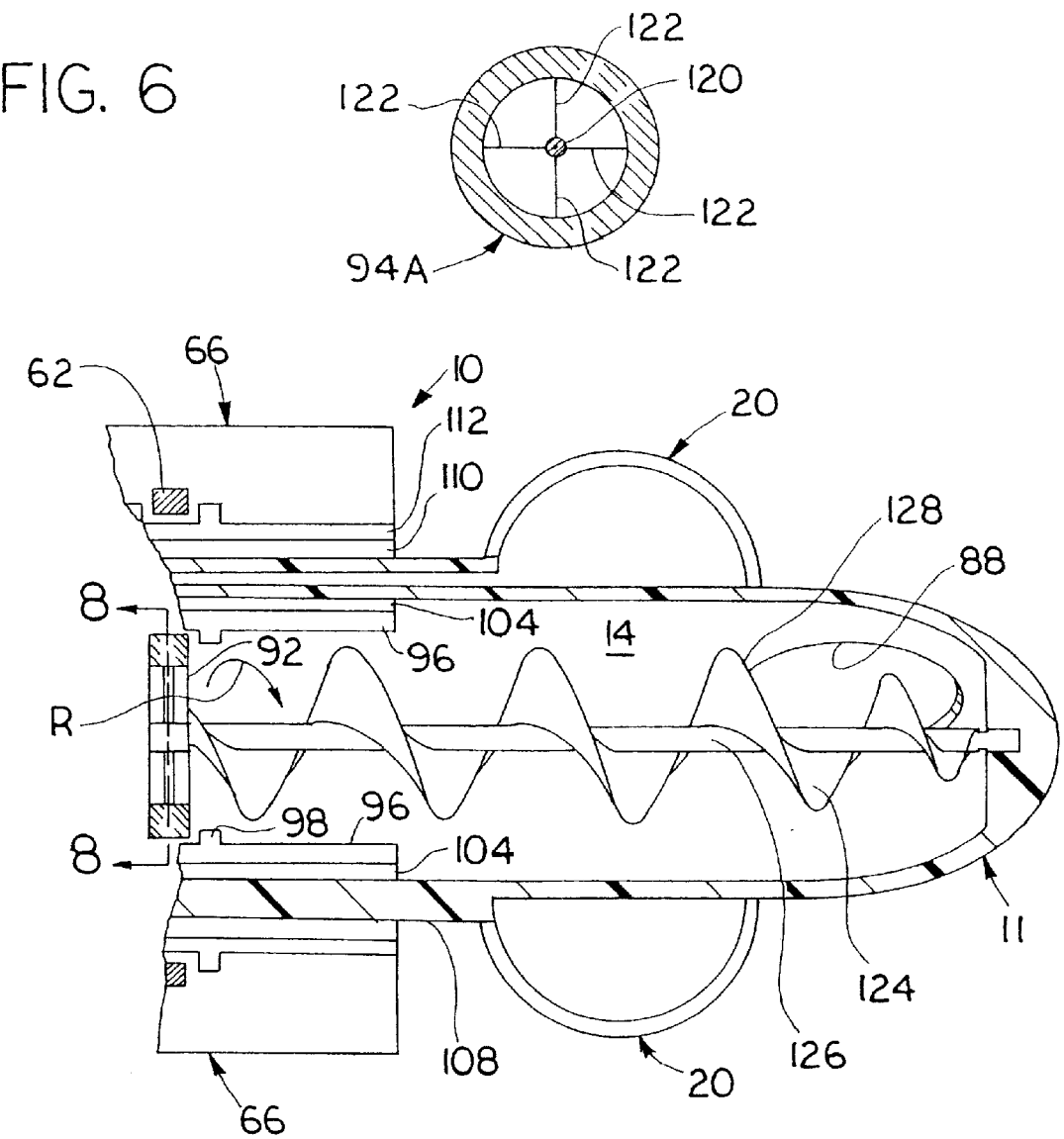

BLADDER DIALYSIS URINARY CATHETER

CROSS-REFERENCE TO RELATED PATENT APPLICATION

This patent application is based on and claims the benefit of the filing date of U.S. provisional patent application 60/053,557 filed Jul. 24, 1997 by James F. McGuckin, Jr., M.D. and entitled "Method and Apparatus for Bladder Irrigation Mechanical Thrombolysis".

BACKGROUND OF THE INVENTION AND DESCRIPTION OF THE PRIOR ART

One of the side effects of many urological procedures is formation of blood clots in the urine within the bladder. Typically after urological procedures the patient will be fitted with a catheter to facilitate bladder drainage. Clots forming in the urine within the bladder tend to clog the inlet orifice for a catheter thereby preventing effective voiding of the bladder. This is a particular problem subsequent to urological procedures such as transectional prostatectomies, radial prostatectomies and nephrolithotomies.

Magnetic coupling in surgical devices is known, being disclosed in U.S. Pat. No. 5,609,602. However, '602 is concerned with a magnetic couple which limits rotation of one element when driven by a second element, incorporating a mechanical stop for the first element allegedly to produce high frequency oscillations in one of the magnetically coupled pair of elements.

SUMMARY OF THE INVENTION

In one of its aspects, this invention provides an irrigating bladder dethrombulator including a housing insertable into the human bladder via the urethra with an outflow conduit therewithin for transporting bodily fluid from the human bladder and a bladder pressurization conduit for transporting fluid into the bladder to increase bladder internal pressure. The dethrombulator preferably includes means connected to the housing located within the outflow conduit and rotatable with respect thereto for mechanically reducing size of clots in the bodily fluid passing through the outflow conduit. The mechanical clot size reducing means is preferably driven by means connected to the exterior of the housing which drives the clot size reducing means via a magnetic coupling upon manual or powered rotation of the drive means. The housing preferably includes at least one aperture proximate the clot size reducing means for influx of bodily fluid from within the bladder into the outflow conduit for dethrombosis of the same as the fluid passes through the outflow conduit to exit the bladder and the housing.

In another embodiment of the invention, the means for mechanically reducing size of clots in bodily fluid traversing the outflow conduit is powered by fluid passage through the pressurization conduit.

In another of its aspects, this invention provides a rotating mechanical thrombectomy device, preferably incorporating a turbine, driven by a hydrostatic, pneumatic or other power source, with rotating or torquing blades to break down and shred clots into smaller clots enabling easier passage of the shredded clots out of the patient, thereby preventing occlusion of the outflow port or ports of a drainage catheter.

In yet another of its aspects this invention provides an irrigating bladder dethrombulator having a housing including an outflow conduit adapted for transporting urine and other bodily fluids out of the human bladder with the outflow conduit having a closed distal end. The dethrombulator thus provided preferably further includes a bladder pressurization fluid conduit for transporting fluid into a human bladder and releasing the fluid thereinto to raise internal pressure within the bladder. The dethrombulator preferably further comprises a balloon control conduit adapted for passage therethrough of air or other gaseous fluid for pressurizing a balloon within the human bladder. The pressurization conduit, the outflow conduit and the balloon control conduit are preferably parallel, with walls of the pressurization and balloon conduits preferably being connected to or even formed in an exterior wall of the outflow conduit.

The dethrombulator preferably further includes at least one clot cutting device such as a blade, vane or wire, rotatably mounted within the outflow conduit proximate the distal end thereof, for reducing size of clots in urine by cutting any clots encountered in the course of rotatably passing in close proximity along the interior wall of the outflow conduit.

The dethrombulator may further preferably include a turbine or vane rotatably mounted on a common shaft with said clot cutting device where the turbine or vane is located within the outflow conduit remote from the distal end of the outflow conduit relative to said cutting blade. The turbine or vane, even though largely positioned within the outflow conduit, preferably has at least tip extremities in fluid communication with the pressurization conduit interior, to rotate responsively to fluid passage through said pressurization conduit and driving said clot cutting device.

The dethrombulator yet further preferably includes a balloon adapted to be in fluid communication with the balloon control conduit and connected to the exterior of the outflow conduit for retaining a distal end of the irrigating bladder dethrombulator within the human bladder to be irrigated and dethrombulated.

The outflow conduit preferably includes at least one aperture in the wall thereof at the location of the clot cutting device for influx of urine and other bodily fluid from within the bladder into the outflow conduit for dethrombosis of the same as the fluid passes the cutting blade in the course of passage through the outflow conduit to exit said bladder.

In another of its aspects, this invention provides a method for irritatingly dethrombulating bladder fluid by inserting an outflow conduit into a human bladder through the urethra, internally pressurizing the bladder and turning mechanical clot size reducing means within the outflow conduit to reduce size of clots in bodily fluid passing out of the bladder via the conduit by rotating magnetically coupled drive means located externally of the outflow conduit. Preferably the rotating is performed manually. The method may further include inflating a balloon within the bladder to increase pressure therewithin and retain the conduit within the bladder and may further yet include internally pressurizing the bladder by introducing fluid thereinto.

In yet another of its aspects, this invention provides a method for irritatingly dethrombulating bladder fluid by inserting an outflow conduit into a human bladder through the urethra, internally pressurizing the bladder, turning a clot cutter mounted within the outflow conduit to reduce size of clots and bodily fluid passing out of the bladder via the conduit, responsive to influx of pressurizing fluid into said bladder.

BRIEF DESCRIPTION OF THE DRAWINGS

FIG. 6 is a sectional view taken at lines and arrows 6—6 in FIG. 5.

FIG. 7 is a partially broken schematic vertical section taken at the same position as FIG. 3, showing a third preferred embodiment of an irrigating bladder dethrombulator in accordance with the invention.

FIG. 8 is a sectional view taken at lines and arrows 8—8 in FIG. 7.

The same reference numerals denote corresponding or functionally equivalent parts in the drawing figures.

DESCRIPTION OF THE PREFERRED EMBODIMENTS

Figure 1:
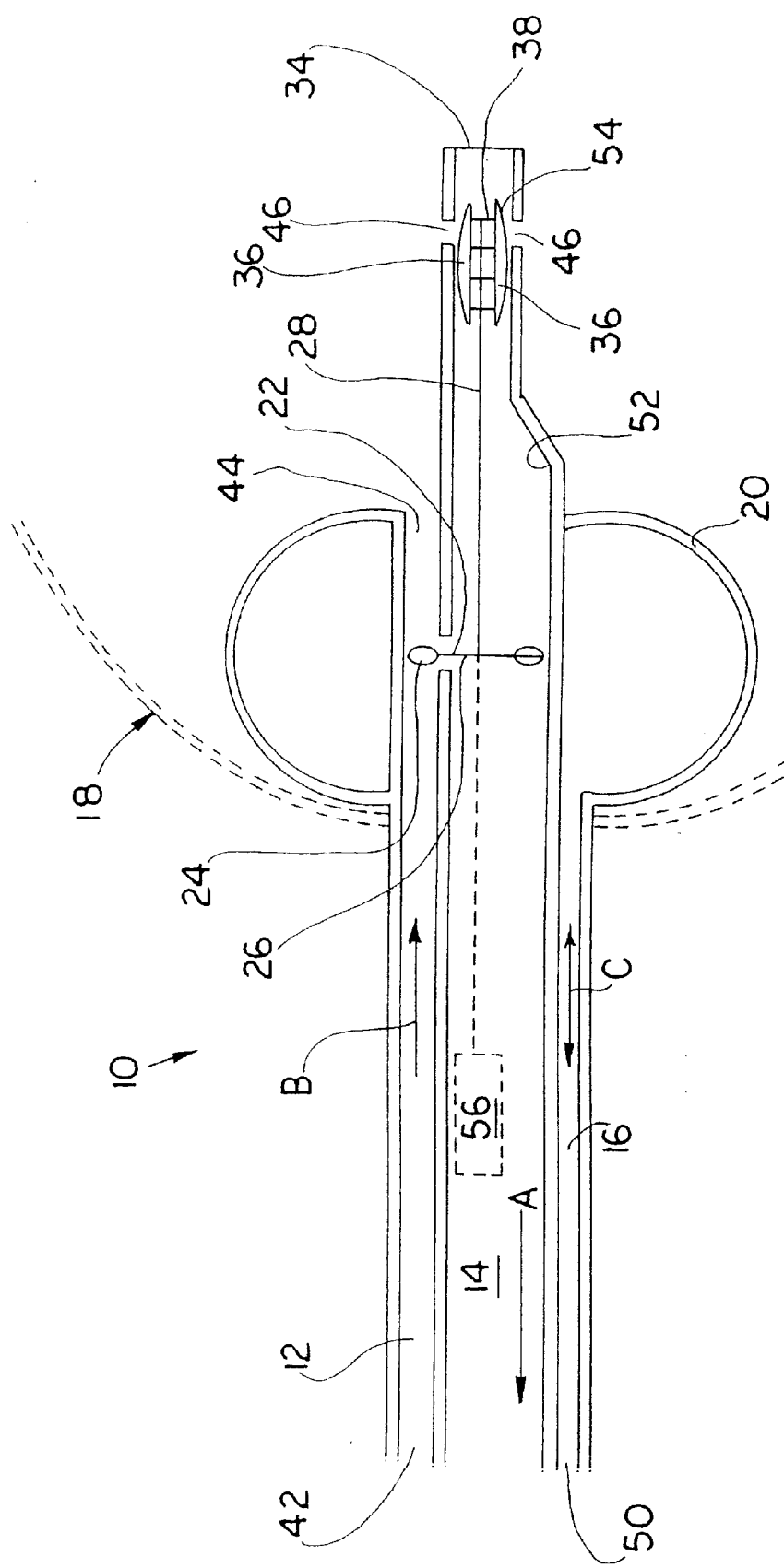
FIG. 1 is a schematic vertical section of one embodiment of an irrigating bladder dethrombulator in accordance with the invention.
Figure 2:
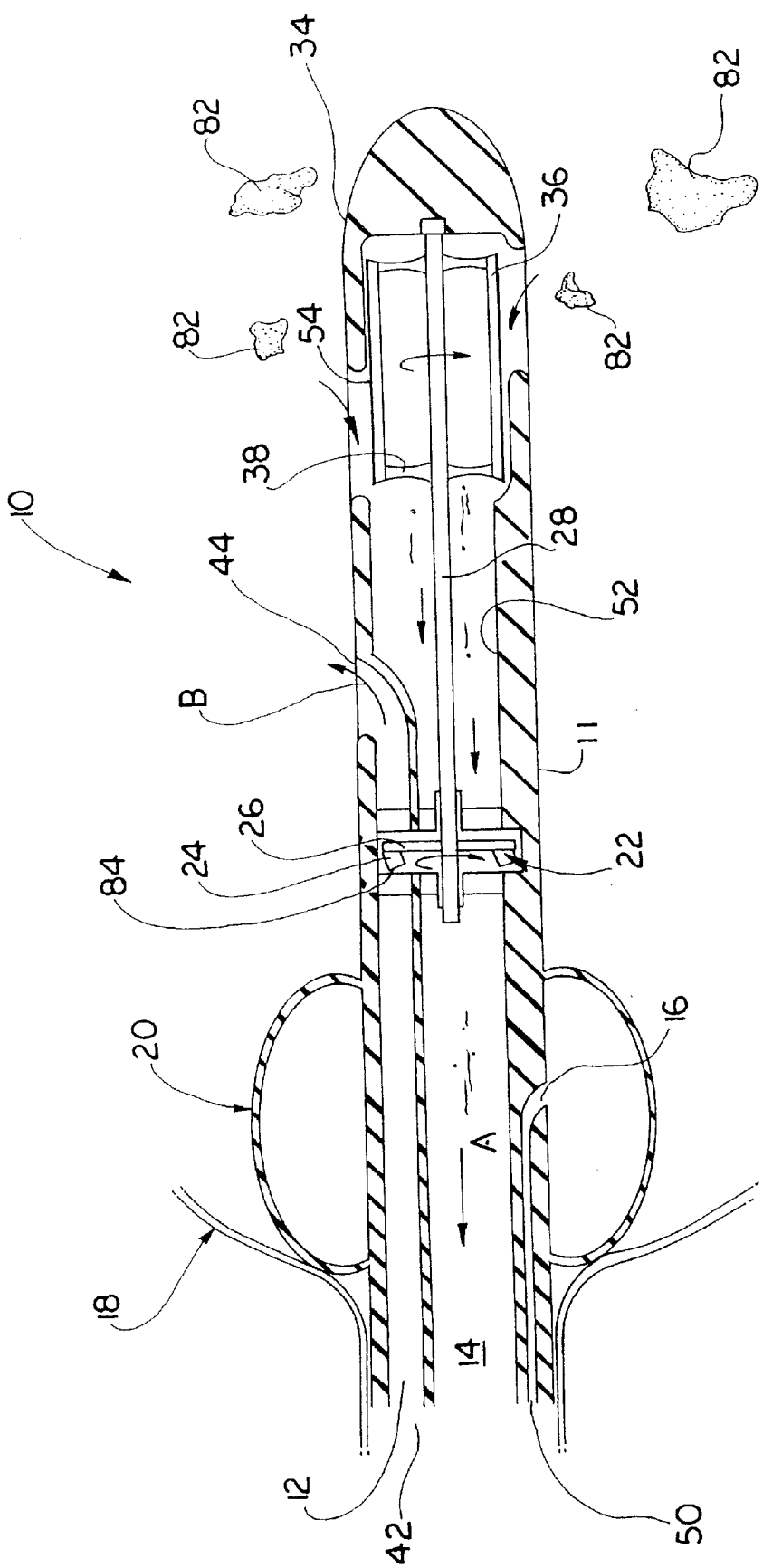
FIG. 2 is a more detailed vertical section of a second embodiment of an irrigating bladder dethrombulator in accordance with the invention.

Referring to FIGS. 1 and 2, irrigating bladder dethrombulators manifesting aspects of the invention and embodying one approach to practice of the invention are illustrated in FIGS. 1 and 2 and generally 10. Dethrombulator 10 generally has a housing 11 which includes an inflow bladder pressurization fluid conduit 12 which is axially elongated as illustrated in FIGS. 1 and 2. Housing 11 further includes a central outflow conduit 14, which is also axially elongated as illustrated in FIGS. 1 and 2, and optimally but preferably a balloon control conduit 16 which is yet additionally axially elongated in the same manner as conduits 12 and 14, all as illustrated in FIGS. 1 and 2.

FIG. 1 illustrates the irrigating bladder dethrombulator in position within a human bladder where the bladder has been designated generally 18 and is illustrated in dotted lines for drawing clarity. In FIG. 2 only a portion of the bladder wall is depicted, without sectioning.

A balloon 20 is preferably attached to the exterior surface of housing 11 as illustrated schematically in FIG. 1 and in FIG. 2. When inflated in place once dethrombulator 10 is within the bladder, balloon 10 helps to retain irrigating bladder dethrombulator 10 in position within bladder 18.

Balloon 20 is in fluid communication with the interior of balloon control conduit 16 so that pressurized air or other gas may be provided to inflate balloon 20 within bladder 18, once the irrigating bladder dethrombulator 10 has been positioned protruding into the bladder via the urethra or, less desirably, through the bladder wall, with pressurized air or other gas being supplied to pressurize balloon 20 via balloon control conduit inlet/exhaust port 50 as illustrated in FIGS. 1 and 2.

Preferably bladder pressurization fluid conduit 12, outflow conduit 14 and balloon control conduit 16 are all parallel one with another. Further preferably walls of the pressurization fluid and balloon conduits are desirably connected to an exterior wall of housing 11 having outflow conduit 14 therewithin in a manner to be immovable with respect thereto.

Pressurization fluid is supplied to the bladder interior via inflow conduit 12, with the fluid entering conduit 12 via bladder pressurization fluid inlet orifice 42 and exiting conduit 12 into bladder 18 via bladder pressurization fluid outlet 44.

In the embodiment of the apparatus illustrated in FIGS. 1 and 2, the dethrombulating function is preferably performed by at least one clot cutting or dethrombulating blade 36, two of which have been illustrated in the drawings. Blades 36 are preferably rotatably mounted within outflow conduit 14 proximate a distal, closed end of outflow conduit 14. The distal, closed end of outflow conduit 14 is designated 34 in the drawings. Clot cutting blades reduce size of clots 82 in urine and other bodily fluid within bladder 18 by slicing any clots 82 which are encountered by blades 36 as those blades rotatably pass in close proximity along the interior wall 52 of outflow conduit 14 in housing 11.

A vane or drive turbine 22 is positioned within outflow conduit 14 remote from the distal end 34 of outflow conduit 14 relative to clot cutting blade 36. Drive turbine or vane 22 is in fluid communication with bladder pressurization fluid conduit 12 and rotates in response to fluid passage through conduit 12. Vane or drive turbine 22 is mounted on a common central shaft 28 with blade 36. Mounting of vane or drive turbine blades 24 on central shaft 28 is accomplished via drive turbine or vane struts 26. While drive turbine 22 is mounted for rotation about central shaft 28 located within the interior of outflow conduit 14, as illustrated in the drawing drive turbine blades 24 protrude through a small aperture 84 formed in wall 52 of outflow conduit 14 so as to be in fluid communication with the interior of conduit 12. Hence, fluid flowing into the bladder through conduit 12 turns central shaft 28 via contact with vane 24.

Dethrombulating blades 36 are mounted via dethrombulating blade struts 38 on central shaft 28 so that dethrombulating blades 36 turn unitarily with and in response to torque provided by drive turbine 22. Dethrombulating blades 36 have their cutting edges 54 located in close proximity to the interior wall 52 of outflow conduit 14, as illustrated. Clots and other debris passing between cutting edges 54 of dethrombulating blades 36 and interior wall 52 of outflow conduit 14 are cut and thereby reduced in size as the fluid medium in which such clots reside is transported out of the bladder through outflow conduit 14, in the direction indicated by arrow A in FIGS. 1 and 2. The direction of flow of the bladder pressurization fluid in conduit 12 is indicated by arrow B in FIGS. 1 and 2. The bi-directional flow of air or other pressurized gas, into or out of bladder 18 through balloon control conduit 16, is indicated by double-ended arrow C in FIG. 1.

While it is envisioned that under normal circumstances sufficient driving torque for operation of dethrombulating blades 36 will be provided via central shaft 28 being rotated by drive turbine or vane assembly 22 in response to pressure from inflow of bladder pressurization fluid in conduit 12 in the direction indicated by arrow B, under certain circumstances it may be desirable to have an auxiliary drive for dethrombulating blades 36.

An auxiliary drive for dethrombulating blades 36 has been illustrated schematically and designated 56 in FIG. 1. Magnetic induction may be used as the auxiliary drive means; magnetic induction has the advantage of not requiring any physical contact and has minimum numbers of moving parts.

Alternatively, a small motor or gear drive can be provided as the auxiliary drive means 56 where the motor can be pneumatically driven, electrically driven or the like.

In any event, regardless of the type of auxiliary drive mechanism used and with or without an auxiliary drive mechanism, the irrigating bladder dethrombulator as illustrated in the drawings should be small and sufficiently flexible to permit passage through the urethra and into the bladder. Hence, rigid structures are desirably to be avoided in the practice of the invention.

Various configurations of dethrombulating blades 36 may be used; it may be desirable to have an auger-type configuration, a ribbon-type configuration or a straight, axially elongated configuration as illustrated specifically in FIG. 1. The blade configuration may depend and may be changed according to the application and the patient in which the irrigating bladder dethrombulator is used.

Figure 3:
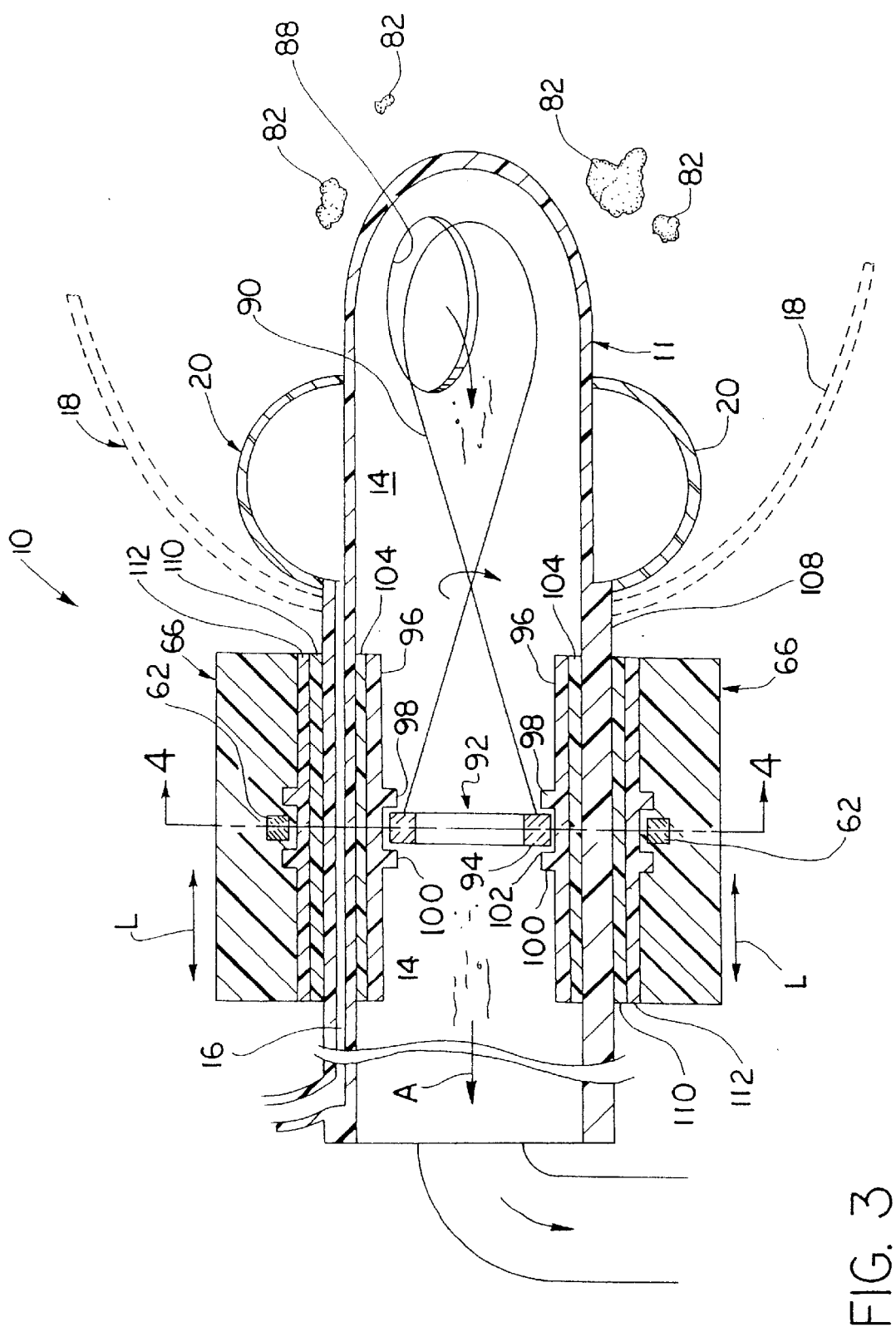
FIG. 3 is a schematic vertical section of a preferred embodiment of an irrigating bladder dethrombulator in accordance with the invention.
Figure 5:
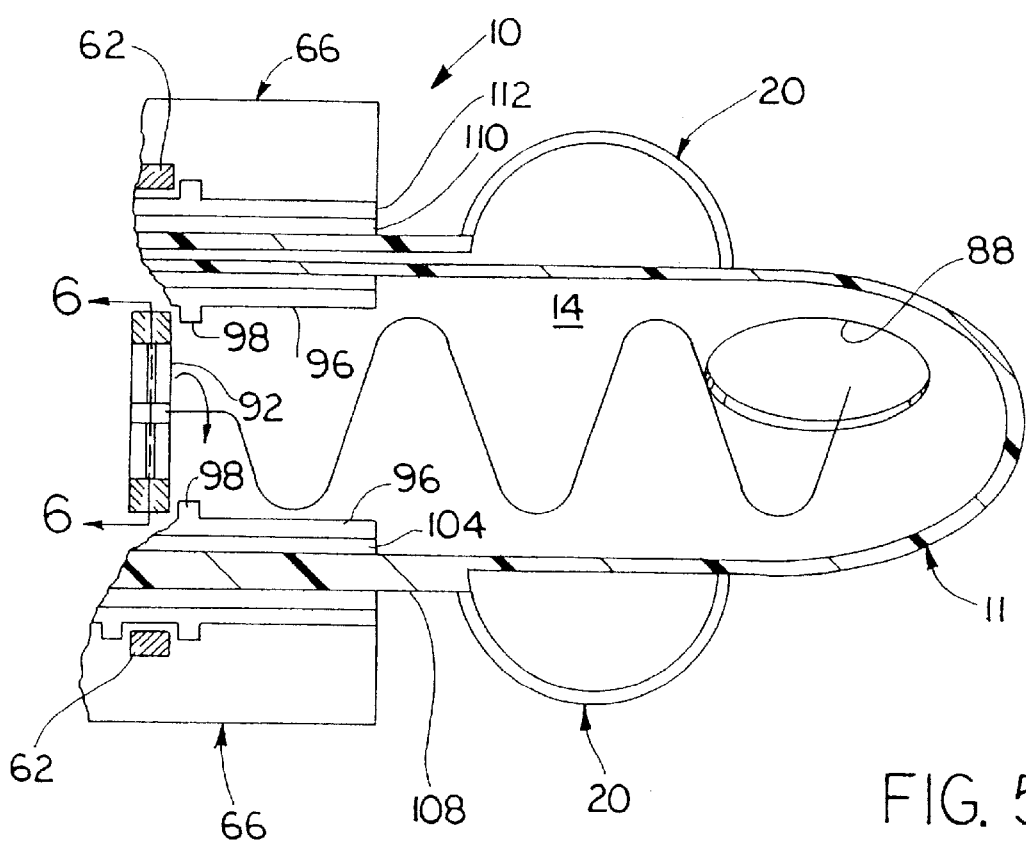
FIG. 5 is a partially broken schematic vertical section taken at the same position as FIG. 3, showing a second preferred embodiment of an irrigating bladder dethrombulator in accordance with the invention.

In one practice of the invention, clot reducing means as represented generally by dethrombulating blades 36 in FIGS. 1 and 2 is rotatably driven by a magnetic coupling with means for magnetically driving the clot cutting means, which drive means are connected to the exterior of the dethrombulator housing as illustrated generally in FIGS. 3, 5 and 8. Referring specifically to FIG. 3, the irrigating bladder dethrombulator according to a preferred embodiment of the invention includes a housing 11 insertable into a human bladder 18. The urethra where the housing includes a outflow conduit 14 for transporting bodily fluid from the human bladder 18 where the outflow conduit 14 has a closed distal end 34 positioned within bladder 18 upon housing 11 being inserted into the bladder. The housing further includes a bladder pressurization conduit 12 for transporting fluid into the bladder interior to increase internal pressure of bladder 18.

Housing 11 includes an aperture 86 which is proximate to the clot size reducing means and permits influx of bodily fluid from within bladder 18 into outflow conduit 14 for dethrombosis of the bodily fluid as the fluid passes through outflow conduit 14 to exit bladder 18 and housing 11.

In the embodiment illustrated in FIG. 3, bladder pressurization fluid conduit 12 for inflow of bladder pressurization fluid is not illustrated in housing 11 in order to assure drawing clarity.

In the embodiment illustrated in FIG. 3, the clot cutting means as provided by a wire 90 formed in a loop with the base of the loop being defined by an annular member 92, which is rotatably disposed within the central portion of outflow conduit 14. Annular member 92 includes means for receiving magnetic flux and rotating annular member 92 in response thereto where the magnetic flux receiving means is preferably in the form of the annular ring illustrated in section in FIG. 4. Most preferably, annular ring 94 include one or more magnet portions.

Annular member 92 resides within a bearing receptacle formed in an annular interior ring 96 where the bearing receptacle or slot is specifically defined between two radially inwardly extending annular step members 98, 100. Annular interior ring 96 preferably extends circumferentially completely around the inside portion of outlet passageway 14 as shown generally in FIG. 4.

Figure 4:
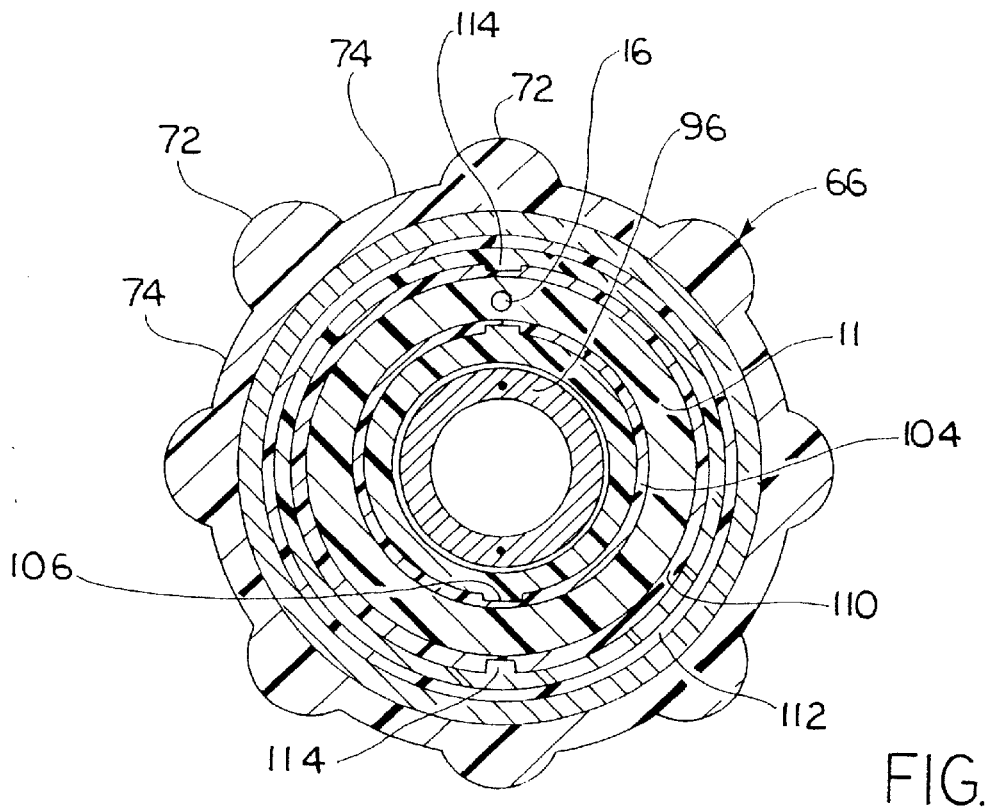
FIG. 4 is a sectional view taken at lines and arrows 4—4 in FIG. 3.

Immediately radially outboard of annular interior ring 96 is an intermediate interior ring 104 which, similarly to annular interior ring 96, extends annularly completely around the circumference of the inside surface of the outflow conduit 14, as also illustrated in FIG. 4. Inner intermediate ring 104 has a pair of axially extending, diametrically opposed keyways, which have not been numbered but are illustrated in FIG. 4, formed therein. These keyways receive corresponding generally rectangular axially extending keys 106 which are diametrically opposite one from another and formed on the outer portion of annular interior ring 96. Keys 106 resident in the unnumbered keyways facilitate longitudinal movement of interior ring 96 and annular magnetic flux receiving ring 94, having annular member 92 rotatably resident therewithin, along the longitudinal axis of outlet flow passageway 14.

Mounted on the exterior surface 108 of housing 11 is an outer inner ring 110 which is preferably fixedly secured to outer surface 108 of housing 11 to be axially immoveable therealong. Similarly to inner intermediate ring 104, outer inner ring 110 has a pair of rectangular, diametrically opposed, longitudinally extending keyways formed therein where these keyways have not been numbered to aid the clarity of the drawing. Annularly disposed about the exterior of outer inner ring 110 is outer intermediate ring 112 which, similarly to annular interior ring 96, has a pair of diametrically opposed longitudinally extending rectangular keys 114 formed therein. Keys 114 fit within corresponding unnumbered keyways formed in outer inner ring 110. Residences of keys 114 in the unnumbered keyways facilitates longitudinal movement of outer intermediate ring 112 along the exterior of housing 11 relative to outer inner ring 110.

Due to the action of keys 114 in the unnumbered keyways, while outer intermediate ring 112 is movably axially respecting outer inner ring 110, these two rings rotate unitarially one with another. Outer intermediate ring 112 is preferably fixably secured to an interior portion of a gripping ring designated generally 66 in FIGS. 3 and 4. Gripping ring 66 has a magnetic member 62 having at least one magnetic as a part thereof, where the magnetic member 62 preferably extends annularly about the complete inner circumference of gripping ring 66 as illustrated in FIG. 4. Gripping ring 66 further includes a plurality of raised portions 72 separated by a plurality of central portions 74 to facilitate hand gripping and hence turning of gripping ring 66, and hence of magnetic member 62, by an attending physician or other health professional. Due to the magnetic coupling provided by close proximity of magnetic member 62 with annular magnetic flux receiving ring 94, rotation of gripping ring 66 produces corresponding rotation of annular magnetic flux receiving ring 95 and hence of annular member 92, resulting in rotation of clot cutting wire 90 within housing 11. Axial movement of gripping ring 66 and the structures associated therewith and the corresponding axial movement of the annular magnetic flux receiving ring 94 relative to housing 11 is indicated by double ended arrows L in FIG. 3.

As a result of the magnetic coupling, manual rotation of gripping ring 66 externally of housing 11 results in rotation of clot cutting wire 64 within housing 11. Clot cutting wire 64 is preferably configured to pass closely about the inner surface 116 of outflow conduit 14 and especially is configured to pass close to inner surface 116 in the vicinity of fluid influx aperture 88 in order to catch and hence slice clots 82 between wire 90 and inner surface 116.

FIGS. 5 and 7 illustrate additional preferred embodiments of the irrigating bladder dethrombulator having the same magnetic coupling structure facilitating manual rotation of gripping rings 66 to rotate annual magnetic flux receiving ring 94, a illustrated in FIG. 3 and described above.

The embodiments illustrated in FIGS. 5 and 7 illustrate alternative clot cutting means in place of clot cutting wire 90 illustrated in FIG. 3.

In FIG. 5, clot cutting means is provided by a rotating wire 118. In the embodiment illustrated in FIG. 5, wire 118 is preferably rotated at a speed sufficient to create a standing wave in wire 118, with at least one node present in the standing wave. As wire 118 is rotated to create the standing wave, longitudinal movement of gripping ring 66 in the direction indicated by arrows L in FIG. 3 results in rotating wire 118, having the standing wave therein, moving longitudinally along interior surface of 116 of outflow passageway 14 in housing 11. This movement of rotating wire 118 permits wire 118 with vibrational nodes therein to move axially along the interior of outflow conduit 118, rotationally slicing clots which are encountered and particularly clots which are trapped between a point of maximum amplitude of rotating wire 118 and interior surface 116 of outflow passageway 14.

When wire 118 is used as the clot cutting mechanism, wire 118 is preferably rotated at a speed at which wire 118 forms at least one vibrational node in the portion of wire 118 extending away from a central hub 120. Wire 118 is preferably hydrophilic, is preferably braided and is preferably rotated in the direction of twist of the braid thereby to provide protection against unraveling of wire 118 when a braided wire is provided.

Central hub 120 is retained in position by radial spokes 122 illustrated in FIG. 6. Annular magnetic flux receiving ring 94A has been so designated in FIG. 6 to distinguish it from annular magnetic flux receiving ring 94 illustrated in FIG. 4. Other than the presence of central hub 120 and spokes 122, annular magnetic flux receiving rings 94, 94A are essentially identical.

In the third preferred embodiment of the invention shown in FIG. 7, the clot cutting means is provided by a spiral, auger-shaped cutting blade 124 mounted on a rotatable shaft 126. Outer edges 128 of spiral clot cutting blade 124 are preferably sharp and pass in close proximity to interior surface 116 of outflow passageway 14 and housing 11 to trap and cut clots 82 therebetween.

As illustrated in FIG. 7, rotatable shaft 126 is preferably journaled in a thickened portion 130 defining a closed distal end of passageway 14.

Similarly to the structure illustrated in FIGS. 3 and 5, a spiral clot cutting blade 124 is mounted in an annular magnetic flux receiving ring 94B illustrated in FIG. 8 and extends from a central hub 130 thereof where central hub 130 is retained in position by radial spokes 132. The preferred direction of rotation of spiral clot cutting blade 124 is denoted by arrow R in FIG. 7.

Similarly to clot cutting wire 90 and wire 118 illustrated in FIGS. 3 and 5, spiral clot cutting blade 124 is preferably longitudinally moveable within housing 11 in the direction indicated by arrows L in FIG. 3, where blade 124 is preferably fixedly connected to annular magnetic flux receiving ring 94B but is slidably moveable along and supported by rotatable shaft 126. Hence blade 124, but not rotatable shaft 126, preferably moves longitudinally in response to longitudinal movement of gripping ring 66 by an attending physician or other health professional.

I claim the following:

1. An irrigating bladder dethrombulator comprising:
   a. a housing insertable into a human bladder via the urethra, including:
      i. an outflow conduit formed therein for transporting bodily fluid out of the human bladder, having a closed distal end;
      ii. a bladder pressurization conduit for transporting fluid into a human bladder to increase bladder internal pressure;
   b. mechanical means within said outflow conduit for reducing size of clots in bodily fluid traversing said outflow conduit;
   c. means rotatably driven by fluid passage through said pressurization conduit for driving said clot size reducing means;
   d. said housing including at least one aperture proximate said clot size reducing means for influx of bodily fluid from within said bladder into said outflow conduit for dethrombosis of the same fluid in the course of fluid passage through said outflow conduit to exit said bladder.

2. The irrigating bladder dethrombulator of claim 1 wherein said housing includes a balloon control conduit for passage therethrough of fluid for internally pressurizing a balloon within said human bladder.

3. The irrigating bladder dethrombulator of claim 2 further comprising a balloon in fluid communication with said balloon control conduit and connected to the exterior of said housing, for retaining a distal end of said housing within said human bladder to be irrigated and dethrombulated.

4. The irrigating bladder dethrombulator of claim 1 wherein said clot size reducing means is rotatably mounted within said outflow conduit.

5. The irrigating bladder dethrombulator of claim 4 wherein said clot size reducing means is rotatably mounted within said outflow conduit proximate the distal end thereof.

6. The irrigating bladder dethrombulator of claim 1 wherein said clot size reducing means further comprises means for cutting clots traversing an interior wall of said outflow conduit.

7. The irrigating bladder dethrombulator of claim 1 wherein said driving means is rotatably mounted on a common shaft with said clot cutting means within said outflow conduit and is rotatably driven by fluid passage through said pressurization conduit.

8. The irrigating bladder dethrombulator of claim 1 wherein said clot size reducing means is a rotating wire.

9. The irrigating bladder dethrombulator of claim 8 wherein said wire is looped.

10. The irrigating bladder dethrombulator of claim 1 wherein said clot size reducing means is a rotatable spiral vane-shaped blade.

11. The irrigating bladder dethrombulator of claim 1 wherein said pressurization conduit, said outflow conduit and said balloon control conduit are parallel.

12. The irrigating bladder dethrombulator of claim 11 wherein internal walls of said housing defining said pressurization and balloon conduits are connected to an exterior wall of said housing and are axially immovable with respect thereto.

13. A method for irrigatingly dethrombulating bladder fluid comprising the steps of:
   a. inserting an outflow conduit into a human bladder;
   b. internally pressurizing said bladder;
   c. turning a clot cutter mounted within said outflow conduit proximate the distal end thereof to reduce size of clots in bodily fluid passing out of said bladder via said conduit;
   d. positioning a vane rotatably mounted on a common shaft with said clot cutter for rotation thereof responsively to influx of pressurizing fluid into said bladder;
   e. permitting bodily fluid flow from within said bladder into said outflow conduit via at least one aperture in the wall thereof proximate said cutter for dethrombosis as said fluid passes said cutter in the course of passage through said outflow conduit to exit said bladder.

14. The method of claim 13 wherein turning said clot cutter within said outflow conduit to reduce size of clots in bodily fluid passing out of said bladder via said conduit is performed by turning a wire at a speed sufficient to create a standing wave in said wire.

15. The method of claim 13 wherein turning said clot cutter within said outflow conduit to reduce size of clots in bodily fluid passing out of said bladder via said conduit is performed by turning spiral shaped blade.

16. The method of claim 13 wherein turning said clot cutter within said outflow conduit to reduce size of clots in bodily fluid passing out of said bladder via said conduit is performed by turning a looped wire.

17. The method of claim 13 further comprising pressurizing said bladder by introducing fluid thereinto.

18. The method of claim 13 further comprising inflating a balloon within said bladder to increase pressure therewithin and retain said conduit within said bladder.

19. The method of claim 13 further comprising cutting clots passing along the interior wall of said outflow conduit.

20. The method for irrigatingly dethrombulating bladder fluid of claim 13 wherein said step of inserting said outflow conduit distal end into a human bladder is performed by inserting said outflow conduit distal end into said bladder via the urethra.

21. The method of claim 18 further comprising maintaining said balloon about the exterior of said outflow conduit thereby retaining a distal end of said irrigating bladder dethrombulator within said human bladder to be irrigated and dethrombulated.

22. A method for irrigatingly dethrombulating bladder fluid comprising the steps of:
   a. inserting an outflow conduit into a human bladder;
   b. internally pressurizing said bladder;
   c. powering clot reducing means mounted said outflow conduit to reduce size of clots in bodily fluid passing out of said bladder via said conduit responsively to influx of pressurizing fluid into said bladder.

23. An irrigating bladder dethrombulator comprising:
   a. a housing insertable into a human bladder via the urethra, including:
      i. an outflow conduit therein for transporting bodily fluid from said human bladder, having a closed distal end positioned within said bladder upon housing insertion thereinto;
      ii. a bladder pressurization conduit for transporting fluid into said bladder to increase bladder internal pressure;
   b. clot reducing means connected to said housing, located within said outflow conduit and rotatable with respect thereto for mechanically reducing size of clots in said bodily fluid passing through said outflow conduit;
   c. means connected to the exterior of said housing and magnetically coupled with said clot reducing means for magnetically driving said clot cutting means;
   d. said housing including at least one aperture proximate said clot size reducing means for influx of bodily fluid from within said bladder into said outflow conduit for dethrombosis of the same as said fluid passes through said outflow conduit to exit said bladder and said housing.

24. The irrigating bladder dethrombulator of claim 23 wherein said driving means further comprises means for generating a magnetic field circumferentially enveloping said clot size reducing means.

25. The irrigating bladder dethrombulator of claim 23 wherein said clot size reducing means rotates upon coaxial rotary motion of said magnetic drive means about said housing.

26. The irrigating bladder dethrombulator of claim 23 wherein said housing further comprises a balloon control conduit for passage therethrough of fluid for inflating a balloon within said bladder and said dethrombulator further comprises:
   a. a balloon communicating with said balloon control conduit and connected to the exterior of said housing, for retaining said housing within said bladder and optionally further pressurizing said bladder.

27. The irrigating bladder dethrombulator of claim 26 wherein said inflow conduit, said outflow conduit and said balloon control conduit are parallel.

28. The irrigating bladder dethrombulator of claim 27 wherein internal walls of said housing defining said inflow and balloon conduits are connected to an exterior wall of said housing and are axially immovable with respect thereto.

29. The irrigating bladder dethrombulator of claim 23 wherein said clot size reducing means is proximate the distal end of said outflow conduit.

30. The irrigating bladder dethrombulator of claim 23 wherein said clot size reducing means cuts clots traveling along an interior wall of said outlet conduit.

31. The irrigating bladder dethrombulator of claim 23 wherein said clot size reducing means is a rotating wire.

32. The irrigating bladder dethrombulator of claim 31 wherein said wire is looped.

33. The irrigating bladder dethrombulator of claim 23 wherein said clot size reducing means is a rotatable spiral vane-shaped blade.

34. A method for irrigatingly dethrombulating bladder fluid comprising the steps of:
   a. inserting an outflow conduit into a human bladder;
   b. internally pressurizing said bladder;
   c. turning mechanical clot size reducing means within said outflow conduit to reduce size of clots in bodily fluid passing out of said bladder via said conduit by rotating magnetically coupled drive means located externally of said outflow conduit.

35. The method of claim 34 wherein said rotating is performed manually.

36. The method of claim 34 further comprising inflating a balloon within said bladder to increase pressure therewithin and retain said conduit within said bladder.

37. The method of claim 34 further comprising internally pressurizing said bladder by introducing fluid thereinto.

38. The method of claim 34 wherein said turning mechanical clot size reducing means within said outflow conduit to reduce size of clots in bodily fluid passing out of said bladder via said conduit is performed by turning a wire at a speed sufficient to create a standing wave in said wire.

39. The method of claim 34 wherein said turning mechanical clot size reducing means within said outflow conduit to reduce size of clots in bodily fluid passing out of said bladder via said conduit is performed by turning a spiral shaped blade.

40. The method of claim 34 wherein said turning mechanical clot size reducing means within said outflow conduit to reduce size of clots in bodily fluid passing out of said bladder via said conduit is performed by turning a looped wire.

* * * * *